US00PP20898P2

(12) United States Plant Patent ter Laak

(10) Patent No.: US PP20,898 P2

(45) Date of Patent: Mar. 30, 2010

(54) *BEGONIA* PLANT NAMED 'ENCANTO ORANGE'

(50) Latin Name: ***Begonia pendula*×*Begonia boliviensis***

Varietal Denomination: Encanto Orange

(75) Inventor: Wendela Antoinette ter Laak, Amstelveen (NL)

(73) Assignee: Beekenkamp Plants B.V., Maasdijk (NL)

( * ) Notice: Subject to any disclaimer, the term of this patent is extended or adjusted under 35 U.S.C. 154(b) by 0 days.

(21) Appl. No.: 12/291,552

(22) Filed: Nov. 12, 2008

(51) Int. Cl.
*A01H 5/00* (2006.01)

(52) U.S. Cl. ..... Plt./343

(58) Field of Classification Search ..... Plt./343
See application file for complete search history.

*Primary Examiner*—Susan B McCormick Ewoldt
(74) *Attorney, Agent, or Firm*—C. A. Whealy

(57) ABSTRACT

A new and distinct cultivar of *Begonia* plant named 'Encanto Orange', characterized by its compact, pendulous and mounded plant habit; freely basal branching habit; and numerous single flowers that are bright orange in color.

1 Drawing Sheet

Botanical designation: *Begonia pendula*×*Begonia boliviensis*.

Cultivar denomination: 'Encanto Orange'.

BACKGROUND OF THE INVENTION

The present invention relates to a new and distinct cultivar of *Begonia* plant, botanically known as *Begonia pendula*× *Begonia boliviensis*, and hereinafter referred to by the name 'Encanto Orange'.

The new *Begonia* plant is a product of a planned breeding program conducted by the Inventor in Amstelveen, The Netherlands. The objective of the breeding program was to develop new hanging *Begonia* cultivars with numerous brightly-colored flowers.

The new *Begonia* plant originated from a cross-pollination made by the Inventor in December, 2006 of a proprietary selection of *Begonia pendula* identified as code number 03-H-27, not patented, as the female, or seed, parent with *Begonia boliviensis* 'Bonfire', disclosed in U.S. Plant Pat. No. 15,108, as the male, or pollen, parent. The new *Begonia* plant was discovered and selected by the Inventor as a single flowering plant from within the progeny of the stated cross-pollination in a controlled greenhouse environment in Amstelveen, The Netherlands in May, 2007.

Asexual reproduction of the new *Begonia* plant by cuttings in a controlled greenhouse environment in Amstelveen, The Netherlands since July, 2007, has shown that the unique features of this new *Begonia* plant are stable and reproduced true to type in successive generations.

SUMMARY OF THE INVENTION

Plants of the new *Begonia* have not been observed under all possible environmental conditions. The phenotype may vary somewhat with variations in environment such as temperature and light intensity, without, however, any variance in genotype.

The following traits have been repeatedly observed and are determined to be the unique characteristics of 'Encanto Orange'. These characteristics in combination distinguish 'Encanto Orange' as a new and distinct cultivar of *Begonia:*

1. Compact, pendulous and mounded plant habit.
2. Freely basal branching habit.
3. Numerous single flowers that are bright orange in color.

Plants of the new *Begonia* can be compared to plants of the female parent selection. Plants of the new *Begonia* differ from plants of the female parent selection in the following characteristics:

1. Plants of the new *Begonia* are more vigorous than plants of the female parent selection.
2. Plants of the new *Begonia* have smaller leaves than plants of the female parent selection.
3. Plants of the new *Begonia* have larger flowers than plants of the female parent selection.
4. Flower color of plants of the new *Begonia* is less intense than flower color of plants of the female parent selection.

Plants of the new *Begonia* can be compared to plants of the male parent, 'Bonfire'. Plants of the new *Begonia* differ from plants of 'Bonfire' in the following characteristics:

1. Plants of the new *Begonia* are not as compact as plants of 'Bonfire'.
2. Leaves of plants of the new *Begonia* are lighter green in color than leaves of plants of 'Bonfire'.
3. Flowers of plants of the new *Begonia* are larger than flowers of plants of 'Bonfire'.
4. Plants of the new *Begonia* and 'Bonfire' differ in flower color as plants of 'Bonfire' have orange red-colored flowers.

Plants of the new *Begonia* can also be compared to plants of the *Begonia* 'Victoria Falls', disclosed in U.S. Plant patent application Ser. No. 12/228,283. In side-by-side comparisons conducted in Amstelveen, The Netherlands, plants of the new *Begonia* differed from plants of 'Victoria Falls' in the following characteristics:

1. Plants of the new *Begonia* were more freely branching than plants of 'Victoria Falls'.
2. Plants of the new *Begonia* had longer and narrower leaves than plants of 'Victoria Falls'.

3. Leaves of plants of the new *Begonia* were glabrous whereas leaves of plants of 'Victoria Falls' were pubescent.
4. Plants of the new *Begonia* had single flowers whereas plants of 'Victoria Falls' had double flowers.
5. Plants of the new *Begonia* had smaller flowers than plants of 'Victoria Falls'.
6. Flowers of plants of the new *Begonia* were lighter in color than flowers of plants of 'Victoria Falls'.

BRIEF DESCRIPTION OF THE PHOTOGRAPH

The accompanying colored photograph illustrates the overall appearance of the new *Begonia* plant, showing the colors as true as it is reasonably possible to obtain in colored reproductions of this type. Colors in the photograph may differ slightly from the color values cited in the detailed botanical description which accurately describe the colors of the new *Begonia.*

The photograph comprises a side perspective view of a typical flowering plant of 'Encanto Orange' grown in a container.

DETAILED BOTANICAL DESCRIPTIONS

Plants used for the aforementioned photograph and following observations and measurements were grown in Amstelveen, The Netherlands in 12-cm containers and under commercial practice in a glass-covered greenhouse during the spring and summer. During the production of the plants, day and night temperatures ranged from 15° C. to 20° C. and maximum light levels were 18,000 lux. Plants had been growing for four months when the photograph and the description were taken. In the following description, color references are made to The Royal Horticultural Society Colour Chart, 2001 Edition, except where general terms of ordinary dictionary significance are used.

Botanical classification: *Begonia pendula*×*Begonia boliviensis* 'Encanto Orange'.

Parentage:

*Female, or seed, parent.*—Proprietary selection of *Begonia pendula* identified as code number 03-H-27, not patented.

*Male, or pollen, parent.*—*Begonia boliviensis* 'Bonfire', disclosed in U.S. Plant Pat. No. 15,108.

Propagation:

*Type.*—By vegetative cuttings.

*Time to initiate roots.*—About 15 days at temperatures of about 20° C.

*Time to produce a rooted young plant.*—About 14 to 18 days at temperatures of about 20° C.

*Root description.*—Medium in thickness, fibrous; white in color; plants of the new *Begonia* have not been observed to form tubers.

*Rooting habit.*—Freely branching; moderately dense.

Plant description:

*Plant form and growth habit.*—Compact, pendulous and mounded plant habit; freely basal branching with about five to six primary branches per plant; primary branches with secondary branches at potentially every node. Moderately vigorous to vigorous and moderate to fast growth rate.

*Plant height.*—About 15 cm to 20 cm.

*Plant width.*—About 35 cm to 40 cm.

*Branch description.*—Length: About 15 cm to 20 cm. Diameter: About 3 mm to 6 mm. Texture: Smooth, glabrous. Color: Close to 173B.

*Leaf description.*—Arrangement: Alternate, simple. Length: About 12 cm to 14 cm. Width: About 4 cm to 5 cm. Shape: Ovate to lanceolate. Apex: Acute. Base: Cordate. Margin: Serrate. Texture, upper and lower surfaces: Smooth, glabrous. Venation pattern: Palmate; reticulate. Color: Developing and fully expanded leaves, upper surface: Close to N134C; venation, close to 134B. Developing and fully expanded leaves, lower surface: Close to 135C; venation, close to 135C. Petioles: Length: About 6 cm to 8 cm. Diameter: About 4 mm. Texture, upper and lower surfaces: Smooth, glabrous. Color, upper surface: Close to 134B. Color, lower surface: Close to 135C.

Flower description:

*Flowering habit.*—Single flowers arranged in cymes. Freely flowering habit with about six to seven open flowers per cyme. Flowers pendulous and face mostly outwardly or downward.

*Fragrance.*—Not detected.

*Natural flowering season.*—Plants flower continuously during the summer in The Netherlands.

*Flower longevity.*—Flowers last about four weeks on the plant; flowers persistent.

*Inflorescence height.*—About 4 cm to 5 cm.

*Inflorescence diameter.*—About 7 cm to 9 cm.

*Flowers.*—Diameter: About 4 cm to 7 cm. Depth (height): About 3 cm to 4 cm.

*Flower buds.*—Shape: Ovoid. Length: About 2 cm to 3 cm. Diameter: About 2 cm to 3 cm. Color: Close to 28B.

*Tepals.*—Arrangement: Rosette. Quantity per flower: Usually about five to seven per flower arranged in a single whorl. Length: About 4 cm to 5 cm. Width: About 2 cm to 3 cm. Shape: Ovate. Apex: Acute. Base: Cordate. Margin: Entire. Texture, upper and lower surfaces: Smooth, glabrous. Color: When opening, upper and lower surfaces: Close to 28B. Fully opened, upper and lower surfaces: Close to 28A; color does not fade with development.

*Flower bracts.*—Quantity/arrangement: Two, opposite. Length: About 1 cm to 2 cm. Diameter: About 1 cm to 2 cm. Shape: Obovate to rounded. Apex: Obtuse. Base: Sagittate. Margin: Entire; undulate. Texture, upper and lower surfaces: Smooth, glabrous. Color, when opening, upper and lower surfaces: Close to 145C; towards the margin, close to 29D. Color, fully opened, upper and lower surfaces: Close to 145D; towards the margin, close to 29C.

*Peduncles.*—Angle: About 30° to 45° from vertical. Strength: Moderately strong. Length: About 5 cm to 6 cm. Diameter: About 4 mm to 5 mm. Texture: Smooth, glabrous. Color: Close to 179B.

*Pedicels.*—Angle: About 90° from the peduncle. Strength: Moderately strong. Length: About 4 cm to 6 cm. Diameter: About 2 mm to 3 mm. Texture: Smooth, glabrous. Color: Close to 172D.

*Reproductive organs.*—Stamens and pistils not observed.

*Seed/fruit.*—Seed and fruit production have not been observed.

Disease/pest resistance: Resistance to pathogens and pests common to *Begonia* has not been observed.

Temperature tolerance: Plants of the new *Begonia* have been observed to tolerate temperatures from about 10° C. to about 40° C.

It is claimed:

1. A new and distinct *Begonia* plant named 'Encanto Orange' as illustrated and described.

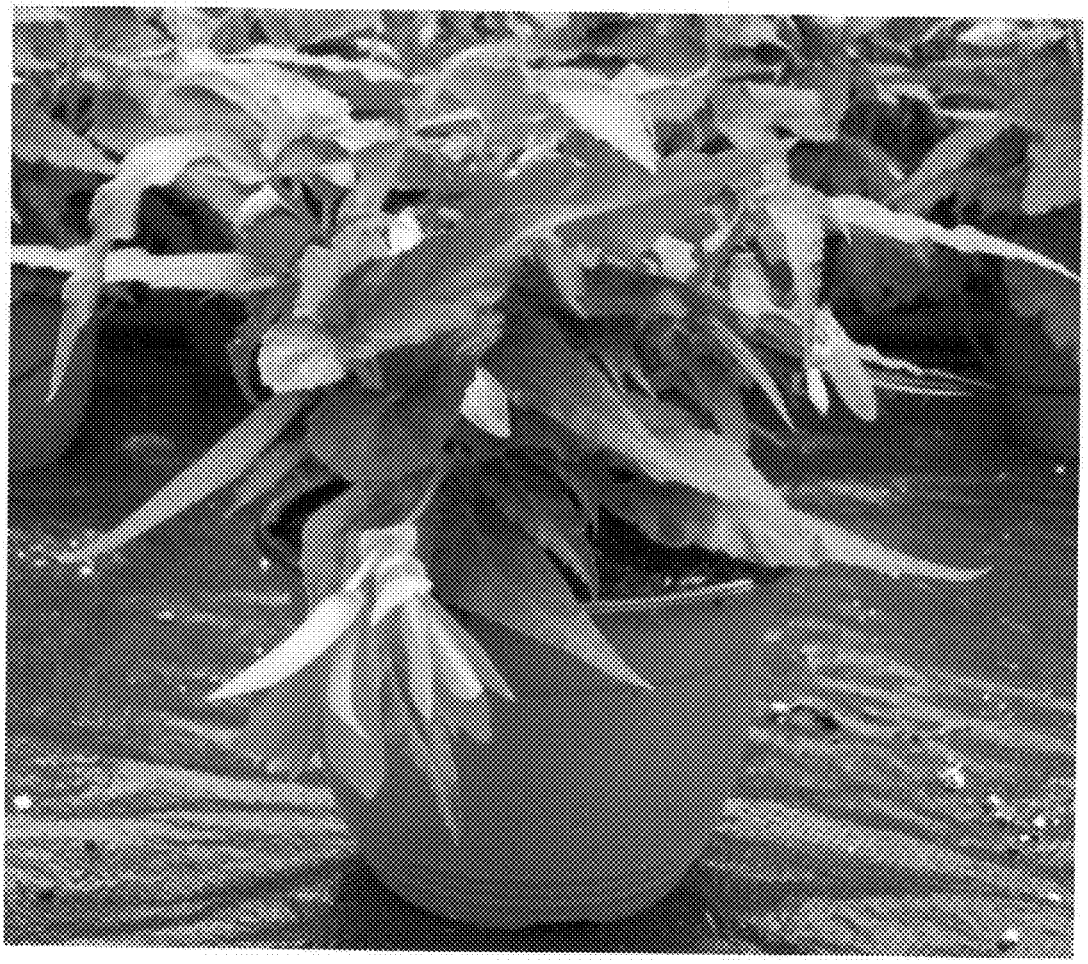

* * * * *